United States Patent
Sesekura

[11] Patent Number: 5,891,053
[45] Date of Patent: Apr. 6, 1999

[54] BLOOD-COLLECTING DEVICE

[75] Inventor: Tetsuya Sesekura, Kanagawa, Japan

[73] Assignee: Kabushiki Kaisya Advance, Tokyo, Japan

[21] Appl. No.: 776,407

[22] PCT Filed: May 22, 1996

[86] PCT No.: PCT/JP96/01354

§ 371 Date: Jan. 27, 1997

§ 102(e) Date: Jan. 27, 1997

[87] PCT Pub. No.: WO96/37148

PCT Pub. Date: Nov. 28, 1996

[30] Foreign Application Priority Data

May 25, 1995 [JP] Japan .................................. 7-149680
May 25, 1995 [JP] Japan .................................. 7-149681

[51] Int. Cl.⁶ .......................................................... A61B 5/00
[52] U.S. Cl. ........................ 600/583; 600/575; 600/577; 600/578
[58] Field of Search .................................. 128/760, 770, 128/765, 763, 762; 606/181, 182, 183; 600/577, 578, 573, 575, 576, 579, 583

[56] References Cited

U.S. PATENT DOCUMENTS

| | | | |
|---|---|---|---|
| 3,623,475 | 11/1971 | Sanz et al. ........................... | 128/770 |
| 4,139,011 | 2/1979 | Benoit et al. ......................... | 606/182 |
| 4,653,513 | 3/1987 | Dombrowski ....................... | 128/765 |
| 5,318,584 | 6/1994 | Lange et al. ......................... | 606/181 |
| 5,368,047 | 11/1994 | Suzuki et al. ....................... | 128/765 |
| 5,680,872 | 10/1997 | Sesekura et al. . | |

FOREIGN PATENT DOCUMENTS

| | | | |
|---|---|---|---|
| 286128 | 3/1935 | Italy ..................................... | 606/183 |
| 7-51251 | 2/1995 | Japan . | |
| 7051251 | 2/1995 | Japan . | |
| 7-132119 | 5/1995 | Japan . | |
| 1080986 | 8/1967 | United Kingdom ................ | 606/183 |

OTHER PUBLICATIONS

Japanese Patent Abstract, Publication No. 253173, Publication Date Aug. 1995, p. 1 (no translation).

*Primary Examiner*—Richard J. Apley
*Assistant Examiner*—Justine R. Yu
*Attorney, Agent, or Firm*—Christie, Parker & Hale, LLP

[57] ABSTRACT

A blood-collecting device includes a suction device for suctioning and thereby swelling a portion of a patient's skin by decompression so that a movable paracentetic needle can be driven into the swollen skin to puncture the skin. Once the skin has been punctured, the paracentetic needle is withdrawn while suction is maintained on the swollen skin in order to draw a blood sample from the patient.

9 Claims, 8 Drawing Sheets

BODY

BODY

BODY

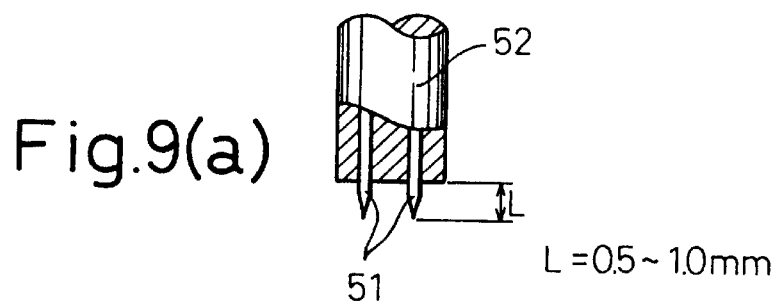
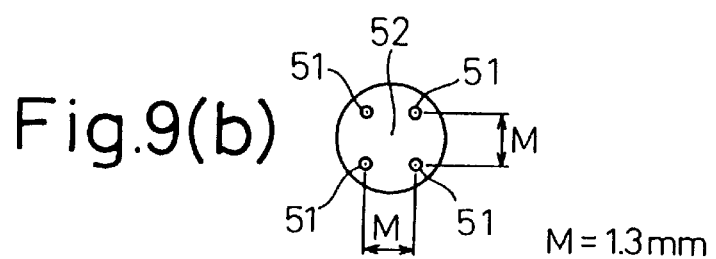
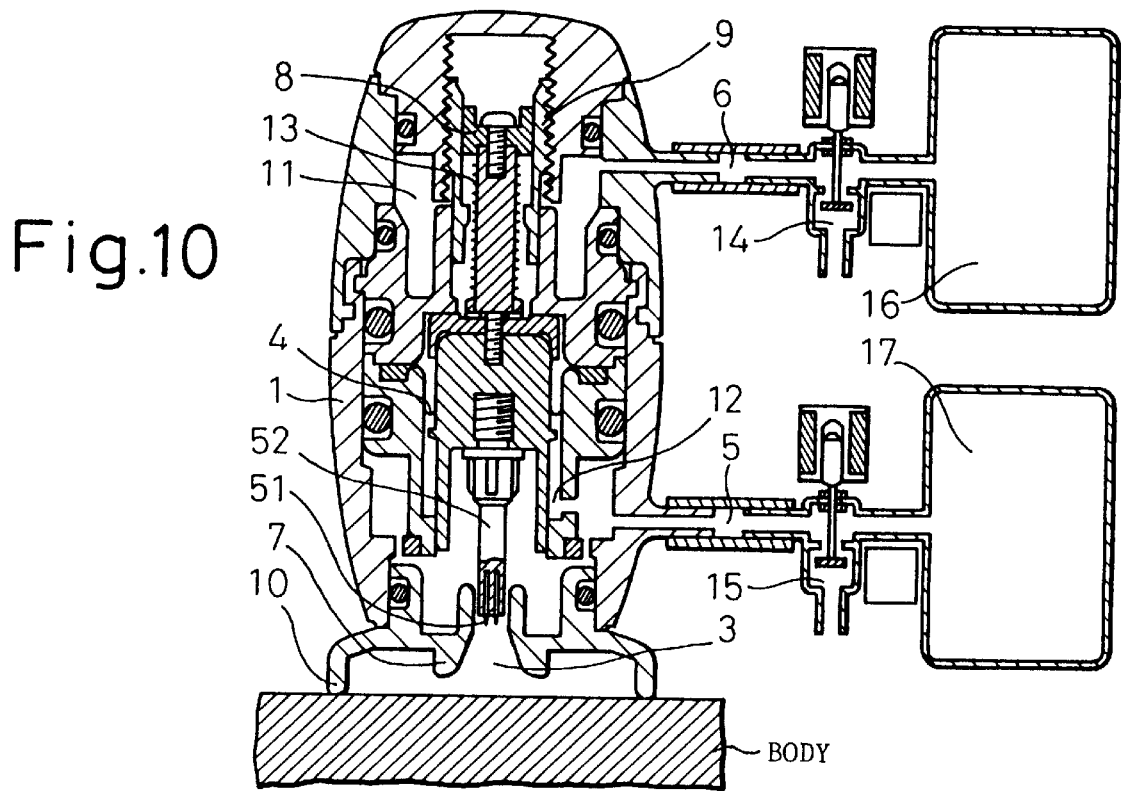

BLOOD-COLLECTING DEVICE

TECHNICAL FIELD

The present invention relates to a blood-collecting device.

BACKGROUND ART

In recent years, which have seen an increase in the number of patients suffering from various adult diseases such as diabetes, believed to be due to changes in eating habits and a greater level of stress, a heavy burden is being imposed on the daily lives of the patients themselves who must make regular visits to the hospital, and therefore as blood sugar tests become an ever more usual part of their daily lives, the procedure of blood collection itself is receiving more attention as an important topic. The problem of the pain accompanying blood collection becomes a more significant issue in cases where the procedure must be repeated, and it is becoming a serious obstacle particularly for insulin-dependent patients, which include a large number of children. Furthermore, blood-transmitted diseases have become a social problem in recent years, and therefore, in the interest of preventing especially serious diseases such as AIDS and hepatitis, a device has been sought which may allow patients to take repeated blood collections by themselves without undue burden; yet, no blood-collecting device has been realized which can satisfy these conditions.

Conventional blood-collecting devices in common use are devices which cause a powerful impact of a small blade into the tip of the finger, cutting the skin and extracting blood, but despite the mere instant of contact between the blade and the skin, the resulting pain is more than imagined and thus its daily use has been quite difficult to sustain.

Incidentally, devices have been proposed which draw blood by first suctioning the skin and then forming a puncture in the suctioned section with a paracentesis needle; however, it is often the case that the amount of blood taken is less than the amount required for the measurement, and this has created uncertainties from the standpoint of stably obtaining reliable blood samples amounts.

DISCLOSURE OF THE INVENTION

In light of these circumstances, the present invention accomplishes reliable collection of blood in a substantially painless manner, by a construction comprising a combination of suction means for suctioning the skin by decompression, paracentetic means for dropping a paracentetic member into the skin in the aforementioned suctioned state to impact the skin, and removal means for drawing out the aforementioned impacted paracentetic member from the skin.

The present invention also accomplishes reliable collection of blood in a substantially painless manner by way of a multiple-needle construction as the paracentetic means.

BRIEF DESCRIPTION OF THE DRAWINGS

FIGS. 9(a) and 9(b) are illustrations of an embodiment of the paracentetic means section of a device according to the invention, with FIG. 9(a) being a side view showing a partial cross-section, and FIG. 9(b) being a front view.

FIG. 10 is an illustration of an embodiment of a device according to the invention.

BEST MODE FOR CARRYING OUT THE INVENTION

Figure 1:
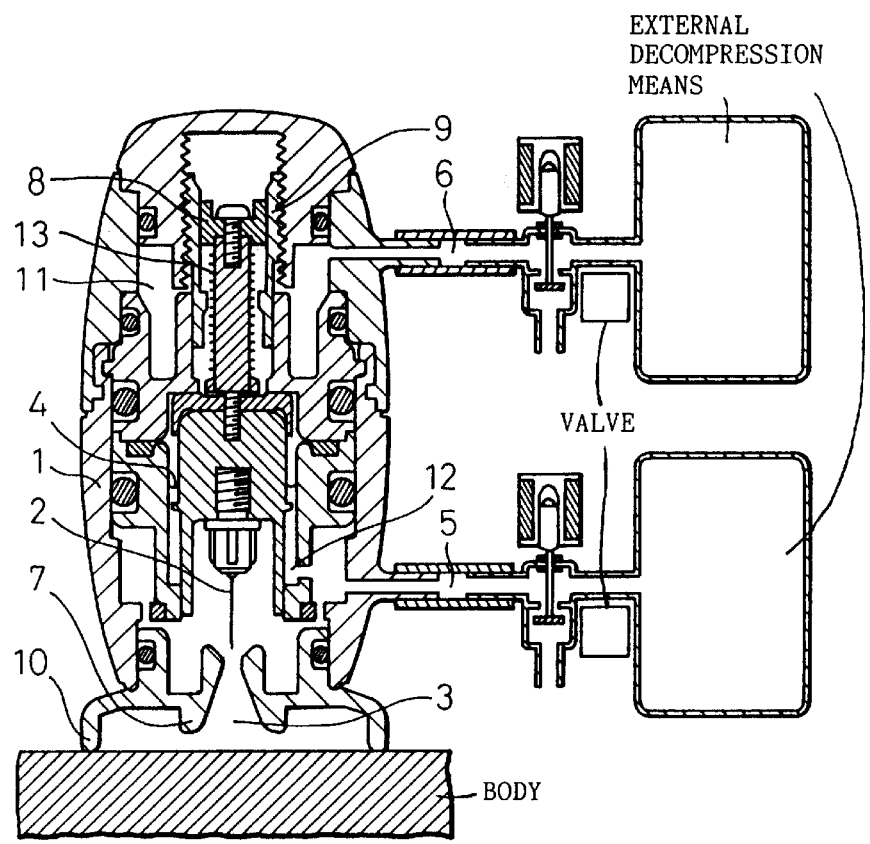
FIGS. 1 and 2 are cross-sectional views of an embodiment of a device according to the invention.

In the above reference to substantial painlessness, the pain is largely affected by the feelings of the person from whom the blood is collected, i.e. by a subjective factor, and therefore it is intended to include small degrees of pain, though lighter than the pain normally associated with blood collection as described above in regard to the prior art, while including a degree of pain which is acceptable on a continuous daily basis.

According to the present invention, the section of the skin subjected to the suction is not restricted and may be the fingertip, upper arm, lower arm, etc., but the upper arm is preferred for its wider surface area.

The suction force indicates the degree to which the skin rises upwards, and is not particularly limited as it depends on the volume of the suction space and the degree of decompression, but an example thereof is a decompression of about −45 kPa to −60 kPa with a gauged pressure where 0 is atmospheric pressure.

The dropping of the paracentetic member refers to the degree of free fall, as well as to cases involving some amount of acceleration or restriction on its drop. The dropping distance is no more than 2 cm, but is otherwise not restricted. Although the subject feels the dropping impact, it is felt as nothing more than a tap or itch. However, since that area of the subject is in a suctioned state and under the application of other forces, the impact is rendered painless.

After dropping, the needle may be held in that state for a few seconds, or it may be immediately drawn out.

As a mode of termination of the paracentesis, the paracentesis needle may be directly drawn out and released from the skin, or its surroundings may be moved so that its relative position is released from the skin, and it is thus removed from the skin.

After the paracentesis needled is removed from the skin, the section of the skin which has been punctured is still in a suctioned state. The suction causes a bodily fluid, which is primarily blood, to be drawn out.

The amount of blood drawn out is generally about 10 µl to 15 µl, but is not restricted to this range.

The continuous operation time from the initial suction until suction after the paracentetic member has been drawn out may be as short as within one minute, or it may be longer depending on other conditions such as the simplicity of the suctioning construction, reduction of the suction force, etc.

The paracentetic member is usually a needle with a core diameter of about 0.3 mm, but it is not necessarily restricted thereto. The member may be, instead of a needle, a blade with an aperture size of 1 mm or less.

A multiple-needle construction used as the paracentetic means of the device according to the invention may consist of an arrangement of needles whose number is not particularly limited, but is preferably from 2 to 6.

The above-mentioned paracentetic means operates in such a manner that it impacts the skin to achieve paracentesis and induce bleeding, or else the skin swollen upon blood congestion caused by suction is brought into contact with the fixed paracentetic means to achieve paracentesis and induce bleeding from the skin, or alternatively the skin is suctioned and the paracentetic means is impacted, or contacted, with the skin which has swollen by blood congestion, to achieve paracentesis and induce bleeding from the skin.

Examples of devices according to the invention will now be explained with reference to the accompanying drawings.

Figure 2:
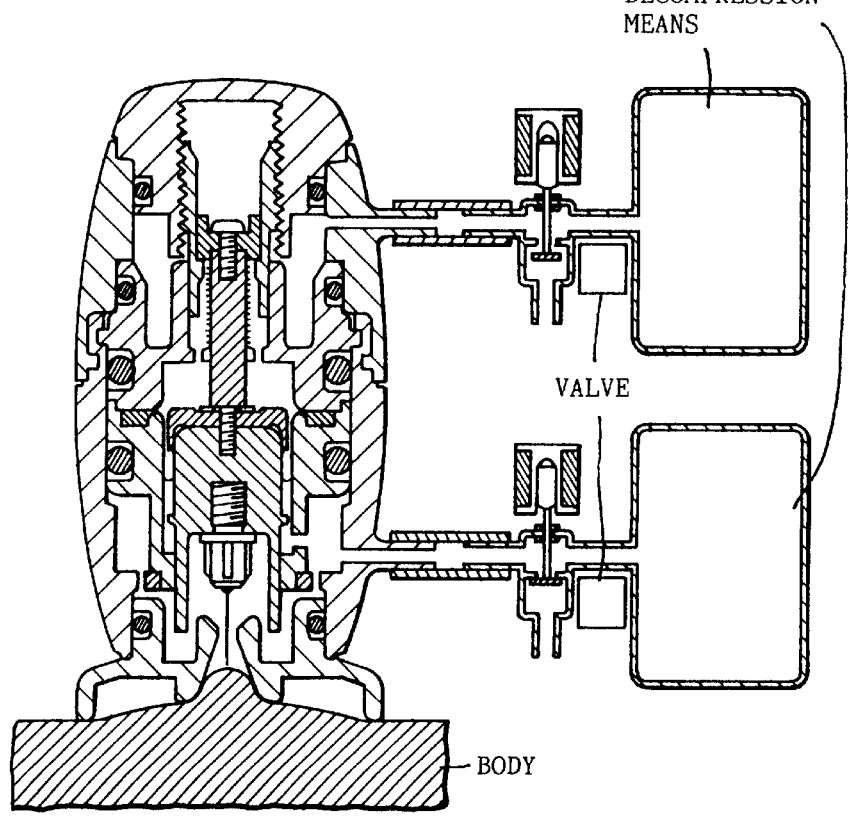

FIGS. 1 and 2 show an embodiment of a device according to the invention. In these figures, 1 is the body, which is divided into an upper air chamber 11 and a lower air chamber 12. Numeral 2 is a paracentetic needle, which has a core diameter of about 0.3 mm. Numeral 3 is a decompression chamber which is roughly cone-shaped and is connected with the lower air chamber 12. Numeral 4 is a diaphragm, and particularly one is used which allows a long displacement of about 10 mm. The diaphragm 4 is formed of a member such as a rubber membrane or synthetic resin membrane which is resilient and flexible. The diaphragm 4 is positioned as a partition between the upper air chamber 11 and lower air chamber 12.

Numeral 5 is a lower decompression opening which serves to connect with external decompression means.

Numeral 6 is an upper decompression opening which serves to connect with external decompression means.

Numeral 7 is an inner ring-shaped protrusion, and 10 is an outer ring-shaped protrusion. This double-protrusion construction prevents obstruction of blood congestion by excess pressure on the skin by the body, while also allowing rapid blood congestion in a concentrated manner in only the very narrow region around the point of paracentesis.

Numeral 8 is a support member, for sliding the paracentetic needle, which is connected to the diaphragm 4 and allows vertical sliding of the paracentetic needle 2. Numeral 9 is an adjusting screw which may be turned to adjust the distance between the paracentetic needle 2 and the skin via the support member 8.

Numeral 13 is a spring with a helical shape. One end of the spring 13 is anchored to the upper air chamber 11 while its other end is mounted on the support member 8, and its discharge force is stored and released upon sliding of the support member 8.

The spring 13 may also be a flat spring, since it is sufficient that force be exhibited upon sliding of the support member 8.

The operation of this device will now be explained in more detail with reference to FIGS. 2, 3(a), 3(b) and 3(c).

Prior to operation, since the upper air chamber 11 and lower air chamber 12 are at atmospheric pressure, the paracentetic needle 2 is held upward by the force of the spring 13, as shown in FIG. 1.

Figure 3A:
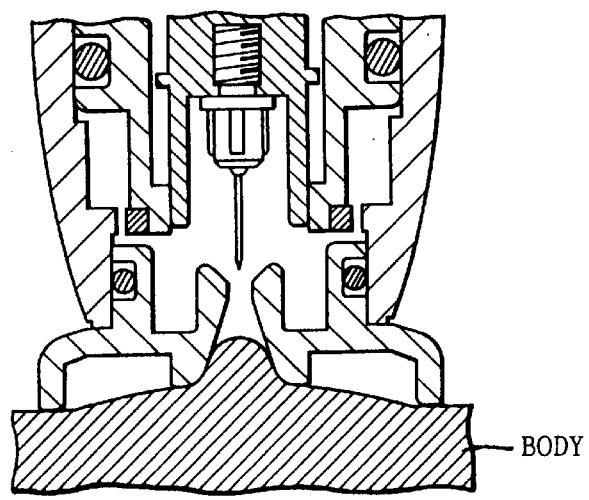
FIGS. 3(a), 3(b) and 3(c) are illustrations of the operation of the device of the aforementioned embodiment.
Figure 3B:
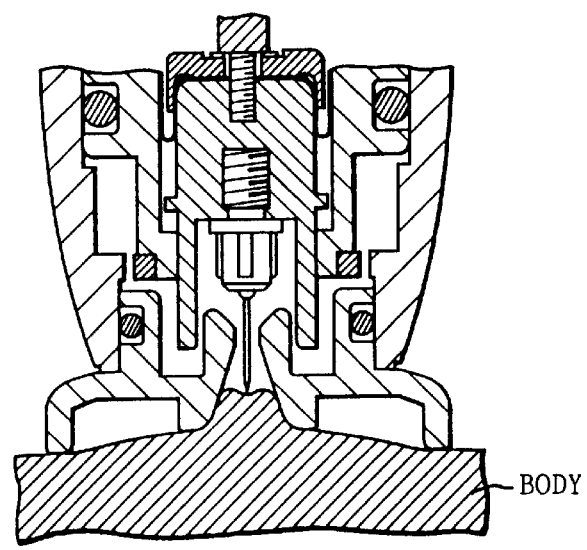

The body 1 is taken by hand, the decompression chamber 3 is contacted with the blood collecting site, and the pressure of the upper air chamber 11 and lower air chamber 12 is lowered to the same degree of decompression by an equal flow acceleration. This decompression causes suction of the skin, inducing swelling of the skin as shown in FIG. 3(a), and thus blood congestion.

After a prescribed period of time has passed, the decompression of the upper air chamber 11 is abruptly attenuated. The reduction in the degree of decompression of the upper air chamber 11 induces a pressure change between the top and bottom sides of the diaphragm 4, and force is applied toward the lower air chamber 12, thus moving the paracentetic needle 2 downward. The paracentetic needle 2 moves with a force corresponding to the difference between the restoring force of the spring 13 and the pressure difference, and thus impacts the skin (FIG. 3(b)).

During this time, the state of decompression of the lower air chamber 12 is maintained. The upper air chamber 11 is then again decompressed until it reaches the same pressure as the lower air chamber 12. Once the pressure difference is eliminated between the lower air chamber 12 and the upper air chamber 11, the restoring force of the spring 13 moves the support member 8 upward, thus releasing the paracentetic needle 2 from the skin.

Figure 3C:
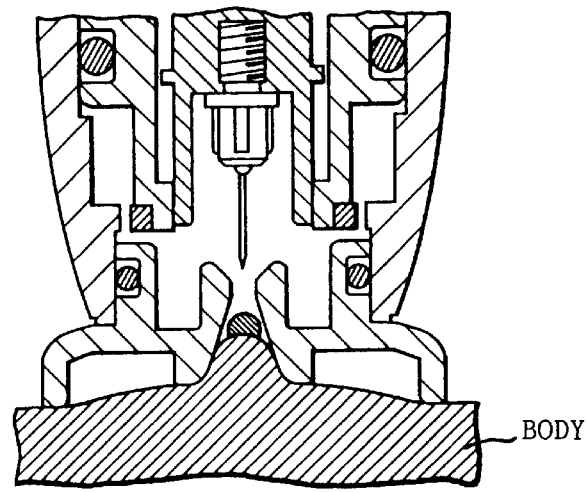

Here, since the lower air chamber 12 is decompressed, further suction causes blood to be drawn from the incision (FIG. 3(c)). The degree of decompression of the lower air chamber 12 at this time is −45 kPa to −60 kPa at a gauged pressure with atmospheric pressure as the zero value.

The explanation given above regards one example of the present invention; the explanation which follows concerns a needle with a shape which induces a lower degree of pain, and it is illustrated in FIGS. 4(a), 4(b), 5(a) and 5(b).

Figure 4A:
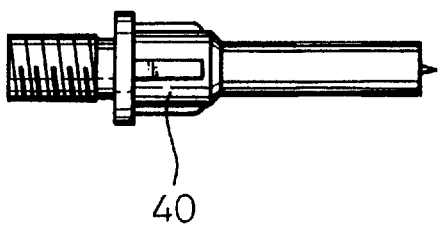
FIGS. 4(a), 4(b), 5(a) and 5(b) are illustrations of an embodiment of paracentetic means used in a device according to the invention.
Figure 4B:
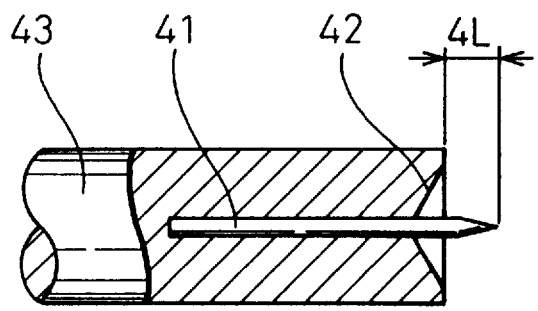

The paracentetic means shown in FIG. 4(a), shown enlarged and in cross sectional view in FIG. 4(b), has an inverted V-shaped surface 42 at the tip of the needle support 43, and a paracentetic needle 41 is situated at the center of the inverted V-shaped surface. The paracentetic needle 41 protrudes a prescribed distance of only 4 L from the tip of the inverted V-shaped surface, and this prescribed distance is ideally, but not necessarily restricted to, about 0.5 mm to 1.5 mm, in consideration of the pain during use and the amount of blood to be drawn out.

When an incision is created in the skin by impact of the paracentetic needle with the skin, the edge of the inverted V-shaped surface of the needle support 43 impacts the skin almost simultaneously with the impact of the paracentetic needle 41 with the skin, and therefore the pain of the prick when the paracentetic needle 41 impacts the skin is alleviated by the mild shock caused by the impact of the edge of the inverted V-shaped surface of the needle support 43.

Figure 5A:
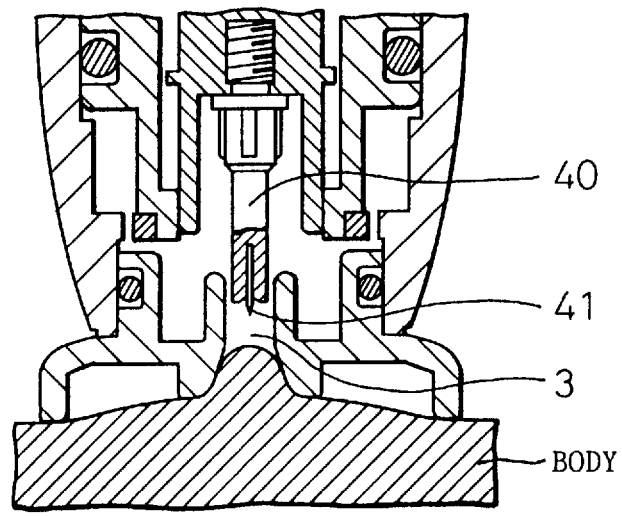
Figure 5B:
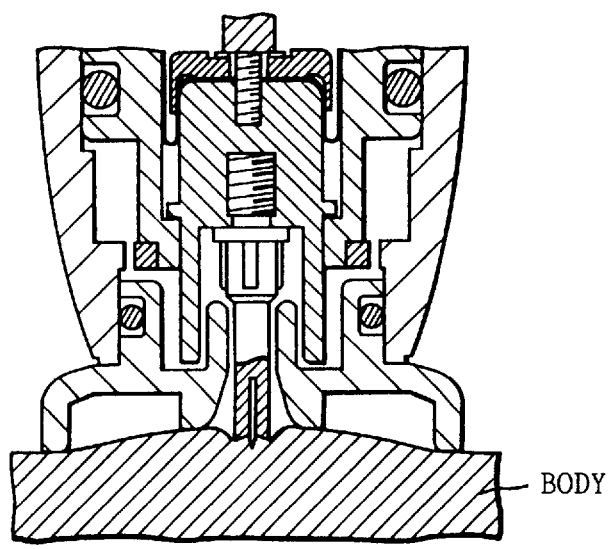

FIGS. 5(a) and 5(b) are partial illustrations of the paracentetic means 40 shown in FIG. 4, corresponding to the example shown in FIG. 1.

Additional paracentetic members will now be explained with reference to FIGS. 6 and 7.

Figure 6A:
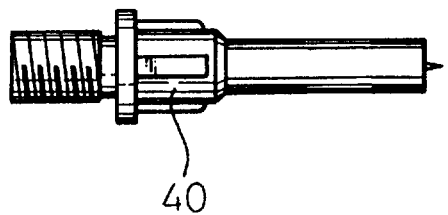
FIGS. 6(a), 6(b), 7(a), 7(b), 8(a), 8(b) and 8(c) are illustrations of another embodiment of paracentetic means used in a device according to the invention.
Figure 6B:
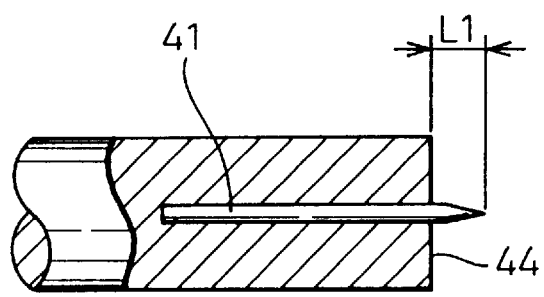

FIGS. 6(a) and 6(b), FIG. 6(b) being an enlarged cross-sectional view of the tip section of FIG. 6(a), show a construction wherein the tip section 44 of the needle support 43 is flat, and the paracentetic needle 41 protrudes from the tip section 44 at a length of a few mm to a few tens of mm.

In this case, if the length L1 of the paracentetic needle 44 protruding from the tip section 44 is less 1 mm or less, the pain incurred upon puncture is minimized, thus realizing a less painful procedure.

Specifically, the pain incurred when the incision is produced in the skin by impact of the paracentetic needle with the skin is proportional to the size of the incision. The size of the incision is defined by both the area and the depth of the incision.

The area of the incision may be adjusted with adequate control by varying the diameter of the paracentetic needle. However, adjustment of the incision depth requires adjustment of a number of factors such as the torque of the paracentetic needle when it impacts the skin, the cutting sharpness of the paracentetic needle, and the movable stroke of the paracentetic needle against different degrees of the suction-induced skin swelling depending on the person. Thus, it has been difficult in the past to control the depth of the incision.

However, according to the present invention, when the needle section of the paracentetic needle has a length of 1 mm or less, the depth of the incision is never greater than 1 mm even without high-precision adjustment of the above-mentioned factors.

Figure 7A:
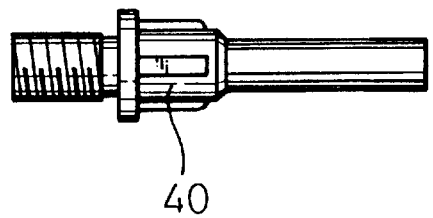
Figure 7B:
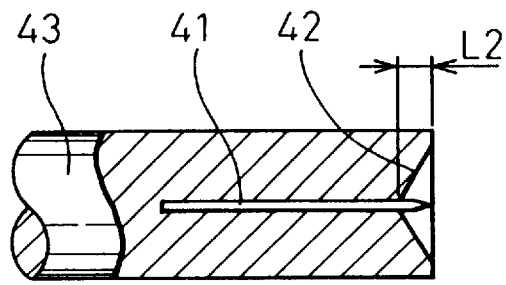

FIGS. 7(a) and 7(b) show another shape for the paracentetic member. The enlarged sectional view in FIG. 7(b) of the paracentetic member in FIG. 7(a) is one with a shortened protruding length L2 of the paracentetic needle 42 of the paracentetic section shown in FIG. 5. L2 is preferably 1 mm or less, so that this shape provides a substantially painless procedure.

Figure 8A:
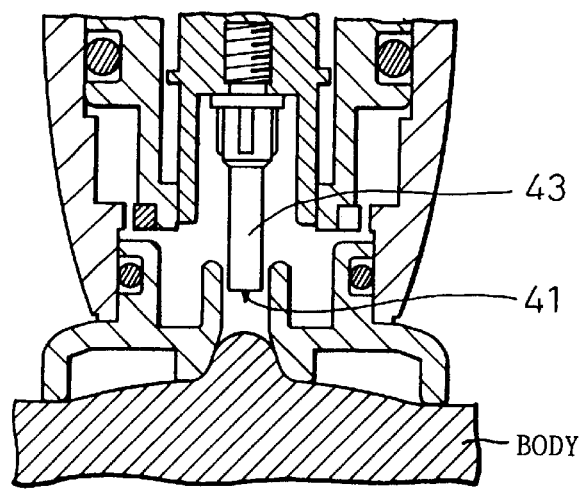
Figure 8B:
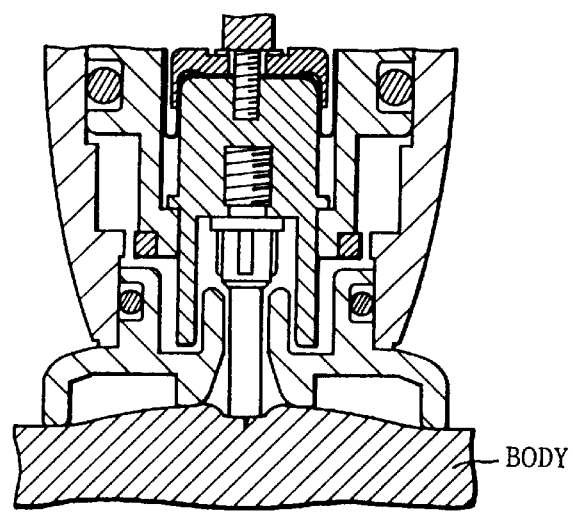
Figure 8C:
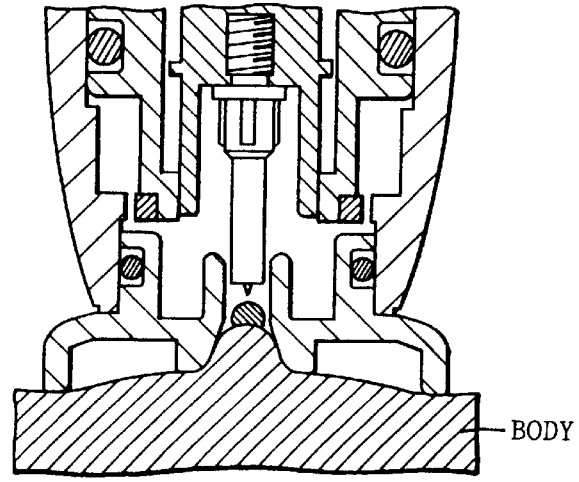

FIGS. 8(a), 8(b) and 8(c) shows an example of the process for taking blood using the paracentetic member shown in FIG. 6.

FIG. 8(a) shows the process of suction, with the blood collection site already suctioned. During the suctioning, the paracentetic member is impacted with the swollen skin (FIG. 8(b)). The paracentetic needle of the paracentetic member punctures the skin, and the paracentesis is then terminated. The suction continues even after the paracentesis has been terminated, thus drawing out blood from the punctured skin (FIG. 8(c)).

FIGS. 9(a) and 9(b) are illustrations of an embodiment of the paracentetic means section used for a device according to the invention.

Numeral 51 indicates paracentetic needles each with a core diameter of about 0.3 mm, and as shown in FIG. 9(b), 4 or them are situated at almost equal spacing on the support 52. If the spacing M is about 1.3 mm, it is possible to obtain a single drop of blood from the incisions created by the paracentetic needles. The heights L of the paracentetic needles 51 are all in the range of about 0.5 mm to 1.0 mm. However, these are only preferred values which are not intended to be restrictive, and they may be appropriately selected depending on the degree of pain felt or the amount of blood to be collected during paracentesis.

FIG. 10 shows the overall construction using the paracentetic means illustrated in FIGS. 9(a) and 9(b).

Numeral 1 is the body which is divided into an upper air chamber 11 and a lower air chamber 12. Numeral 51 indicates the paracentetic needles, 4 of which are arranged as illustrated in FIGS. 9(a) and 9(b). Numeral 3 is a decompression chamber, which is roughly cylindrical and is connected with the lower air chamber 12. Numeral 4 is a diaphragm, and particularly is one which allows a long displacement of about 10 mm. The diaphragm 4 is formed of a member such as a rubber membrane or synthetic resin membrane which is resilient and flexible. The diaphragm 4 is positioned as a partition between the upper air chamber 11 and lower air chamber 12.

Numeral 5 is a lower decompression opening which serves to connect with external decompression means 17. Numeral 6 is an upper decompression opening which serves to connect with external decompression means 16. The decompression means 16 and upper decompression opening 6 are connected by a valve 14, and the decompression means 17 and lower decompression opening 5 are also connected by a valve 15. The valves 14 and 15 are electromagnetic valves, which are opened and closed by input of electrical signals.

Numeral 7 is an inner ring-shaped protrusion, and 10 is an outer ring-shaped protrusion. This double-protrusion construction prevents obstruction of blood congestion by excess pressure on the skin by the body.

Numeral 8 is a support member for sliding of the paracentetic needle, which is connected to the diaphragm 4 and supports vertical sliding of the paracentetic needle 52. Numeral 9 is an adjusting screw which may be turned to adjust the distance between the paracentetic needle 51 and the skin via the support member 8.

Numeral 13 is a spring with a helical shape. One end of the spring 13 is anchored to the upper air chamber 11 while its other end is mounted on the support member 8, and its discharge force is stored and released upon sliding of the support member 8.

The spring 13 may also be a flat spring, since it is sufficient that force be exhibited upon sliding of the support member 8.

Figure 11A:
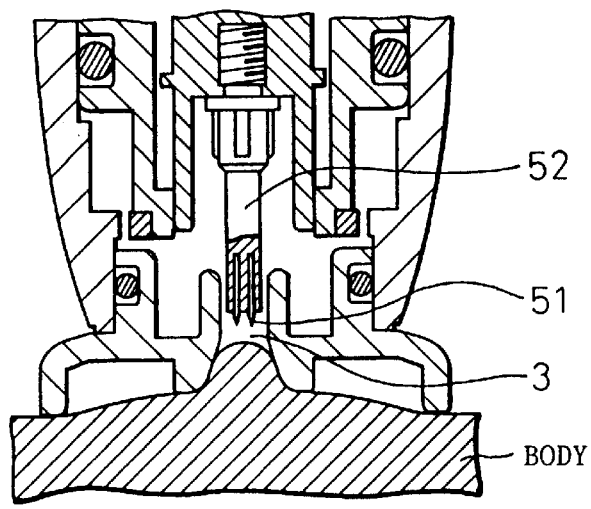
FIGS. 11(a), 11(b) and 11(c) are illustrations of the operation of the device of the aforementioned embodiment.
Figure 11B:
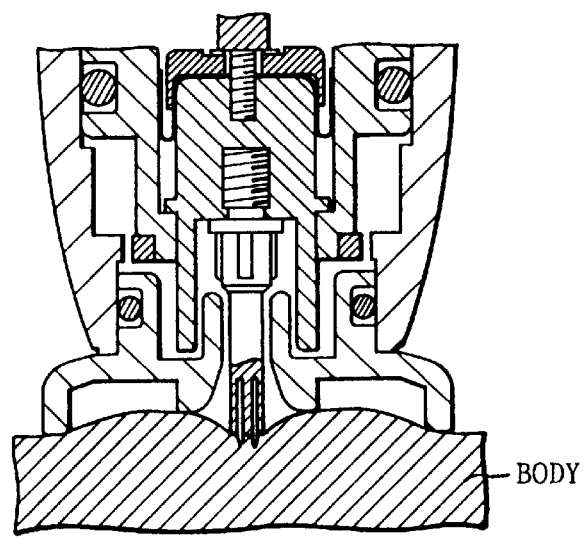

The operation will now be explained in more detail with reference to FIGS. 11(a), 11(b) and 11(c).

Prior to operation, since the upper air chamber 11 and lower air chamber 12 are at atmospheric pressure, the paracentetic needle 51 is held upward by the force of the spring 13, as shown in FIGS. 9(a) and 9(b).

The body 1 is taken by hand, the decompression chamber 3 is contacted with the blood collecting site, and the pressure of the upper air chamber 11 and lower air chamber 12 is lowered to the same degree of decompression by an equal flow acceleration. This decompression causes suction of the skin, inducing swelling of the skin as shown in FIG. 11(a), and thus blood congestion.

After a prescribed period of time has passed, the decompression of the upper air chamber 11 is abruptly attenuated. The reduction in the degree of decompression of the upper air chamber 11 induces a pressure change between the top and bottom sides of the diaphragm 4, and force is applied toward the lower air chamber 12, thus moving the paracentetic needle 51 downward. The paracentetic needle 51 moves with a force corresponding to the difference between the restoring force of the spring 13 and the pressure difference, and thus impacts the skin (FIG. 11(b)).

At this time, the state of decompression of the lower air chamber 12 is maintained. The upper air chamber 11 is then again decompressed until it reaches the same pressure as the lower air chamber 12. Once the pressure difference is eliminated between the lower air chamber 12 and the upper air chamber 11, the restoring force of the spring 13 moves the support member 8 upward, thus releasing the paracentetic needle 51 from the skin.

Figure 11C:
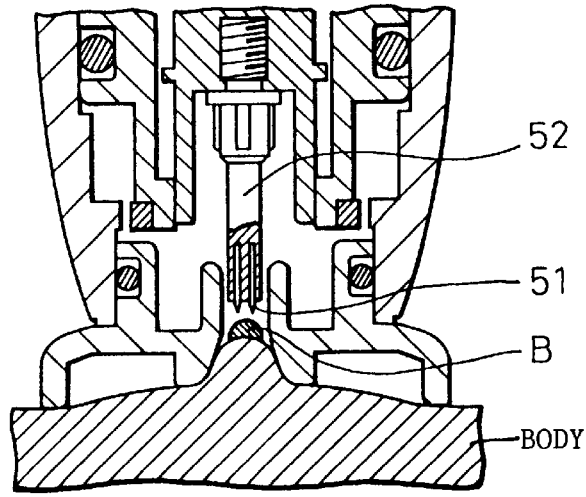

Here, since the lower air chamber 12 is decompressed, further suction causes blood to be drawn from the incision (FIG. 11(c)). The degree of decompression of the lower air chamber 12 at this time is −45 kPa to −60 kPa at a gauged pressure with atmospheric pressure as the zero value.

INDUSTRIAL APPLICABILITY

According to the present invention there is provided a highly useful blood-collecting device with which it is possible to ensure a reliably stable amount of blood collection in a substantially painless manner, and which is simple to operate and may thus be easily used to collect blood at home.

I claim:

1. A blood-collecting device which comprises:

suction means for suctioning a blood collection site of a patient's skin to induce swelling of the skin by decompression, a moveable paracentetic member, means for moving the paracentetic member toward the swollen skin to impact and puncture the skin, and removal means for moving the paracentetic member away from the skin, wherein the suction means further permits blood to be drawn from the punctured skin.

2. A device according in claim 1, wherein said decompression is in a range of −45 kpa to −60 kPa gauge pressure.

3. A device according to claim 1 wherein the paracentetic member comprises a plurality of paracentetic needles.

4. A device according to claim 3, wherein the paracentetic member comprises from 2 to 6 paracentetic needles.

5. A device according to claim 1 wherein the paracentetic member comprises a single paracentetic needle.

6. A device according to claim 1, wherein the paracentetic member comprises a needle support having a flat tip surface and a needle protruding from tip surface.

7. A device according to claim 6, wherein the paracentetic needle protrudes a length of not more than 1 mm from the flat tip surface.

8. A device according to claim 1, wherein the paracentetic member comprises a needle support having an inverted V-shaped tip surface ad a needle protruding from the inverted V-shaped tip surface.

9. A device according to claim 8, wherein the paracentetic needle protrudes a length of not more than 1 mm from the inverted V-shaped tip surface.

\* \* \* \* \*